(12) United States Patent
Jalota et al.

(10) Patent No.: US 8,409,538 B2
(45) Date of Patent: Apr. 2, 2013

(54) TRICALCIUM PHOSPHATE COARSE PARTICLE COMPOSITIONS AND METHODS FOR MAKING THE SAME

(75) Inventors: Sahil Jalota, Santa Clara, CA (US); David C. Delaney, Capitola, CA (US); Duran N. Yetkinler, San Jose, CA (US)

(73) Assignee: Skeletal Kinetics LLC, Cupertino, CA (US)

( * ) Notice: Subject to any disclaimer, the term of this patent is extended or adjusted under 35 U.S.C. 154(b) by 783 days.

(21) Appl. No.: 12/328,720

(22) Filed: Dec. 4, 2008

(65) Prior Publication Data

US 2010/0143480 A1    Jun. 10, 2010

(51) Int. Cl.
*C04B 12/02* (2006.01)
*C01B 25/00* (2006.01)
*A61F 2/28* (2006.01)
*A61K 9/14* (2006.01)

(52) U.S. Cl. ........................................... 423/308

(58) Field of Classification Search .................. None
See application file for complete search history.

(56) References Cited

U.S. PATENT DOCUMENTS

| | | | |
|---|---|---|---|
| 2,735,823 A | 2/1956 | Barrett | |
| 4,859,383 A * | 8/1989 | Dillon | 264/43 |
| 5,032,552 A | 7/1991 | Nonami et al. | |
| 5,679,294 A * | 10/1997 | Umezu et al. | 264/628 |
| 5,683,667 A * | 11/1997 | Fulmer et al. | 423/311 |
| 5,939,039 A | 8/1999 | Sapieszko et al. | |
| 5,968,253 A | 10/1999 | Poser et al. | |
| 5,997,624 A | 12/1999 | Chow et al. | |
| 6,334,891 B1 | 1/2002 | Constantz et al. | |
| 6,558,709 B2 | 5/2003 | Higham | |
| 7,175,858 B2 * | 2/2007 | Constantz et al. | 424/602 |
| 7,294,187 B2 | 11/2007 | Chow et al. | |
| 7,416,602 B2 | 8/2008 | Murphy et al. | |
| 7,527,687 B2 | 5/2009 | Genge et al. | |
| 7,892,346 B2 | 2/2011 | Insley et al. | |
| 7,892,347 B2 | 2/2011 | Insley et al. | |
| 2001/0021389 A1 | 9/2001 | Starling et al. | |
| 2003/0049329 A1 | 3/2003 | Lee et al. | |
| 2004/0005592 A1 | 1/2004 | Emtage et al. | |
| 2004/0029699 A1 | 2/2004 | Lemaitre et al. | |
| 2004/0250730 A1 | 12/2004 | Delaney et al. | |
| 2005/0009176 A1 | 1/2005 | Constantz | |
| 2005/0058717 A1 | 3/2005 | Yetkinler et al. | |
| 2005/0260278 A1 | 11/2005 | Constantz et al. | |
| 2006/0213398 A1 * | 9/2006 | Barralet et al. | 106/690 |
| 2006/0225621 A1 | 10/2006 | Insley et al. | |
| 2006/0292200 A1 | 12/2006 | Delaney | |
| 2007/0189951 A1 | 8/2007 | Constantz et al. | |
| 2008/0028992 A1 | 2/2008 | Lee et al. | |
| 2010/0249794 A1 | 9/2010 | Moseley et al. | |
| 2010/0269736 A1 | 10/2010 | Chow et al. | |
| 2011/0073006 A1 | 3/2011 | Jalota et al. | |
| 2012/0024195 A1 | 2/2012 | Shoji | |
| 2012/0031305 A1 | 2/2012 | Shoji | |

OTHER PUBLICATIONS

Takagi et al. (Biomaterials, 19, published 1998, p. 1593-1599).*
Wang et al. (Journal of Materials Science Materials in Medicine, 4, published 1993, p. 150-158).*
Thangamani et al. (Ceramics International, 28, published 2002, p. 355-362).*

* cited by examiner

*Primary Examiner* — Fereydoun G Sajjadi
*Assistant Examiner* — Alma Pipic
(74) *Attorney, Agent, or Firm* — Bret E. Field; Benjamin C. Pelletier; Bozicevic, Field & Francis LLP (57) ABSTRACT

Methods for preparing a tricalcium phosphate coarse particle composition are provided. Aspects of the methods include converting an initial tricalcium phosphate particulate composition to hydroxyapatite, sintering the resultant hydroxyapatite to produce a second tricalcium phosphate composition and then mechanically manipulating the second tricalcium phosphate composition to produce a tricalcium phosphate coarse particle composition. The subject methods and compositions produced thereby find use in a variety of applications.

19 Claims, 9 Drawing Sheets

TRICALCIUM PHOSPHATE COARSE PARTICLE COMPOSITIONS AND METHODS FOR MAKING THE SAME

Calcium phosphate cements find use as structural materials in the orthopedic and dental fields. Such cements are typically prepared by combining a dry component(s) and a liquid to form a flowable paste-like material that is subsequently capable of setting into a solid calcium phosphate product. Materials that set into solid calcium phosphate mineral products are of particular interest as such products can closely resemble the mineral phase of natural bone and are susceptible to remodeling, making such products extremely attractive for use in orthopedics and related fields. While a large number of different calcium phosphate cement formulations have been developed, there is a continued need for the development of yet more advanced formulations.

SUMMARY

Methods for preparing a tricalcium phosphate coarse particle composition are provided. Aspects of the methods include converting an initial tricalcium phosphate particulate composition to hydroxyapatite, sintering the resultant hydroxyapatite to produce a second tricalcium phosphate composition and then mechanically manipulating the second tricalcium phosphate composition to produce a tricalcium phosphate coarse particle composition. The subject methods and compositions produced thereby find use in a variety of applications.

DETAILED DESCRIPTION

Methods for preparing a tricalcium phosphate coarse particle composition are provided. Aspects of the methods include converting an initial tricalcium phosphate particulate composition to hydroxyapatite, sintering the resultant hydroxyapatite to produce a second tricalcium phosphate composition and then mechanically manipulating the second tricalcium phosphate composition to produce a tricalcium phosphate coarse particle composition. The subject methods and compositions produced thereby find use in a variety of applications.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject methods will be described first, followed by a description of the compositions produced thereby, kits for use in preparing the same and methods for using the subject compositions in methods of hard tissue, e.g. bone repair.

Tricalcium Phosphate Coarse Particle Compositions and Methods of Making the Same As summarized above, the invention provides methods of preparing tricalcium phosphate coarse particle compositions. In methods of the invention, an initial tricalcium phosphate composition is first converted to hydroxyapatite. Tricalcium phosphate is a compound with formula $Ca_3(PO_4)_2$. It is also known as calcium orthophosphate, tertiary calcium phosphate, tribasic calcium phosphate, or "bone ash". Tricalcium phosphate has β-phase (low temperature phase), γ-phase (high pressure phase), and α-phase (high temperature phase).

In certain embodiments, tricalcium phosphate used in the present methods has an alpha crystal form or a beta crystal form. Alpha-tricalcium phosphate ($\alpha$-TCP) is a high-temperature and beta-tricalcium phosphate ($\beta$-TCP) is a low-temperature polymorph In a certain instances, the initial tricalcium phosphate particulate composition is obtained from commercial sources. VITOSS® tricalcium phosphate composition is composed of $\beta$-TCP and can be purchased from Orthovita (Malvern, Pa.). Other commercial sources of tricalcium phosphate include Curasan (Research Triangle Park, N.C.), Depuy Spine (Mountain View, Calif.), and Teknimed (L'Union, France).

Alternatively, the initial tricalcium phosphate composition may be synthesized denovo. Any convenient synthesis protocol may be employed. In one instance, the initial tricalcium phosphate composition is prepared by combining DCPA, calcite and water to produce a paste composition; sintering the paste composition to produce a sintered product; and then mechanically disrupting the sintered product to produce the initial tricalcium phosphate particulate composition. DCPA is dicalcium phosphate, anhydrous and can be purchased commercially from Mutchler Inc. (Harrington Park, N.J.), Fuji Health Science (Burlington, N.J.), and JRS Pharma (Patterson, N.J.). Calcite is a carbonate mineral and a stable polymorph of calcium carbonate ($CaCO_3$). Calcite can be purchased commercially from Ashirwad Minerals and Marbles (India) and Britex Enterprises (Delhi, India), In methods of the invention, the initial tricalcium phosphate composition is converted to hydroxyapatite. While any convenient protocol may be employed, in some instances conversion of the initial tricalcium phosphate composition to hydroxyapatite is accomplished by combining the initial tricalcium phosphate composition with an alkali metal phosphate solution. Suitable alkali metal counterions include sodium, potassium, and lithium. Suitable alkali metal phosphate solutions of interest include sodium phosphate, sodium phosphate dibasic, sodium phosphate monobasic, potassium phosphate, potassium phosphate dibasic, and potassium phosphate monobasic. In a certain instance, the alkali metal phosphate solution is a sodium phosphate solution, such as $NaH_2PO_4$.

The initial tricalcium phosphate composition and alkali metal phosphate solution may be combined using any convenient protocol. As such, a volume of the solution may be combined with an amount of the dry initial tricalcium phosphate composition with mixing to produce a paste composition which sets into hydroxyapatite. Mixing may be manual or automated. Drying may occur at room temperature or at elevated temperatures.

Following production of the hydroxyapatite, the resultant hydroxyapatite is then milled or pelletized. Accordingly, in some embodiments the hydroxyapatite is milled before sintering. Milling techniques include use of jet mill, disc mill, blender, homogenizer, serrated disc type agitator, pearl mill, high speed impeller mill, ball mill, sand mill, attritor, rotor stator mixer and the like. In some instances, the hydroxyapatite is disc milled before sintering. In yet other embodiments, the hydroxyapatite is pelletized before sintering. Pelletizing is the process of compressing or molding of a product into the shape of a pellet and can be performed with a pellet mill. A pellet mill is a type of mill used to create cylindrical pellets from a mixture of dry powder and a wet ingredient. The pellets are made by compacting the material into many small holes in a die. The die is usually round and the pellets are pushed from the inside out. Pellet mills combine small materials into a larger, homogeneous mass. The pelletizing process can include the use of heat and pressure.

Following conversion of the initial tricalcium phosphate composition to hydroxyapatite and subsequent processing as desired (e.g., milling or pelletizing as reviewed above), the resultant hydroxyapatite is sintered to produce a second tricalcium phosphate composition. Sintering is a method where material is heated below its melting point until its particles adhere to each other. Sintering may be performed at atmospheric or elevated pressure, as desired. In certain embodiments, sintering occurs at temperatures ranging from 1300-1500° C., such as at temperatures of 1300° C., 1350° C., 1400° C., 1425° C., 1450° C., and 1500° C. In one instance, sintering occurs at 1400° C. In another instance, sintering occurs at 1425° C. In another instance, sintering occurs at 1450° C.

As summarized above, sintering results in the production of a second tricalcium phosphate composition. The resultant second tricalcium phosphate composition is then mechanically manipulated to produce a tricalcium phosphate coarse particle composition. Mechanical manipulation may vary, where mechanical manipulation may be achieved by disc milling and sieving. Pulverizing systems with one or more disc mill assemblies as known in the art may be employed. In some instances, the pulverizing system includes feeding input material to the disc mill, carrying ground material from the disc mill to a sorting module, transporting acceptable ground material to a ground material collection area, and recirculating unacceptable ground material to a disc mill for further grinding. A disc mill can include a spindle, a flywheel, a rotating disc blade, a stationary disc blade, a means for cooling the stationary disc blade (e.g., a waterjacket), a means for introducing air into the mill, and a means for adjusting a gap between facing cutting surfaces of the disc blades. An example of a pulverizing system using a disc mill is described in WO 2004/071666.

Other methods of mechanical manipulation include blender, homogenizer, serrated disc type agitator, pearl mill, high speed impeller mill, ball mill, sand mill, attritor, rotor stator mixer and the like. Specific speed characteristics depend on equipment, blade configuration, size, etc., but can be determined readily by one skilled in the art.

Methods of the invention are high yield methods with respect to the production of coarse tricalcium phosphate particles. The methods of the invention can yield a composition that is 50% or more coarse particles, such as 60% or more coarse particles, including 80% or more coarse particles by number.

Coarse tricalcium phosphate particles produced in accordance with methods of the invention are particles that are 20 µm in diameter or larger, such as ranging in size from 38 to 212 µm in diameter. In certain embodiments, the method produces a tricalcium phosphate coarse particle composition that comprises particles ranging in size from 38 to 106 µm. In another embodiment, the method produces a tricalcium phosphate coarse particle composition that comprises particles ranging in size from 106 to 212 µm.

The method produces tricalcium phosphate coarse particles comprising an alkali metal ion in an amount ranging from 1500 to 2500 ppm. In certain embodiments, the particles comprise an alkali metal ion in an amount ranging from 1500 to 2400 ppm, 1600 to 2400 ppm, 1600 to 2200 ppm, or 1600 to 2000 ppm. The alkali metal ion can be sodium, potassium, or lithium. The alkali metal ion can come from the alkali metal phosphate solution that is used to form hydroxyapatite.

Coarse particle compositions having a high amount of coarse particles, e.g., 50, 60, 80% or more as reviewed above, may be further processed as desired. For example, the desired tricalcium phosphate coarse particles (for example those particles ranging in size from 38 to 212 μm in diameter) may be separated from the remainder of the composition using any convenient separation protocol, such as sieving, etc.

Calcium Phosphate Cements and Methods of Using the Same

Coarse tricalcium phosphate particles of the invention find use in a variety of different applications where tricalcium phosphate is desired as a reactant. One application of interest includes the use of the tricalcium phosphate coarse particle compositions in calcium phosphate cements formulated for use in medical and dental applications.

Of particular interest is the use of the tricalcium phosphate coarse particles of the invention in a cement that is made up of a dry reaction composition which includes both the coarse particles of the invention, e.g., as described above, and a fine particle component. In these types of cements, the dry reactants include the a tricalcium phosphate coarse particle composition that has mean particle size that is at least 2 times larger than the mean particle size of the fine particles component, where the mean particle size of coarse particle component may be 20 μm or larger, 30 μm or larger, 40 μm or larger (as determined using the Horiba LA-300 laser diffraction particle sizer (Version 3.30 software for Windows 95)(Irvine, Calif.)), such as 50 μm or larger, 100 μm or larger, 150 μm or larger, 200 μm or larger, where the particle size of the tricalcium phosphate coarse particle component population (also referred to herein as a coarse particle size population) may range from 10 to 500 μm, such as from 25 to 250 μm. In certain instances, the particles of this component can range in size from 38 μm to 212 μm, such as from 38 μm to 106 μm or 106 μm to 212 μm.

As indicated above, also present in cements of these embodiments is a fine particle composition component which is a calcium and/or phosphate dry reactant having a mean particle size (as determined using the Horiba LA-300 laser diffraction particle sizer (Version 3.30 software for Windows 95)(Irvine, Calif.)) of less than 8 μm and a narrow particle size distribution (which is referred to below as a fine particle size population). As such, the dry reactant component of the cement, which may include one or more distinct dry reactants, includes a reactant that has a mean particle size of less than 8 μm and a narrow particle size distribution. The mean particle size of this reactant may vary, ranging in representative embodiments from 1 to 7 μm, such as from 1 to 6 μm, including from 1 to 5 μm, where the mean particle size in certain embodiments may be 1, 2, 3 and 4 μm, where in certain embodiments the mean particle size is 3 μm.

There is also a narrow particle size distribution. By narrow particle size distribution is meant that the standard deviation of the particles that make up the particular reactant population (as determined using the Horiba LA-300 laser diffraction particle sizer (Version 3.30 software for Windows 95)(Irvine, Calif.)) does not exceed 4.0, and in certain representative embodiments does not exceed 3.0, e.g., does not exceed 2.5, including does not exceed 2.0 μm. The fine particle component is further characterized in that the mode (as determined using the Horiba LA-300 laser diffraction particle sizer (Version 3.30 software for Windows 95)(Irvine, Calif.)) does not exceed 8.0, and in certain representative embodiments does not exceed 6.0, e.g., does not exceed 5, including does not exceed 3.0 μm.

In certain embodiments, the fine particle composition is a calcium phosphate compound having a calcium to phosphate ratio ranging from 1.0 to 2.0, including from 1.33 to 1.67, such as 1.5. In certain embodiments, the calcium phosphate compound is a tricalcium phosphate, such as α- and β-tricalcium phosphate, where in certain embodiments, the tricalcium phosphate is α-tricalcium phosphate.

In certain embodiments, the amount of the fine particle component of the dry reactant composition is greater than the total amount of other reactant components that may be present, such as the tricalcium phosphate coarse particle composition component as described herein. In these embodiments, the mass ratio of the fine particle component to the total mass of the dry reactants may range from 1 to 10, e.g., from 9 to 6, such as from 9 to 7, including from 9.5 to 8.5.

The ratios or relative amounts of each of the disparate calcium and/or phosphate compounds in the dry reactant mixture is one that provides for the desired calcium phosphate product upon combination with the setting fluid and subsequent setting. In many embodiments, the overall ratio (i.e., of all of the disparate calcium and/or phosphate compounds in the dry reactants) of calcium to phosphate in the dry reactants ranges from 4:1 to 0.5:1, usually from 2:1 to 1:1 and more usually from 1.9:1 to 1.33:1.

The coarse and fine particle size populations may be made up of the same or different compounds, e.g., the same or different calcium minerals, such as the same or different calcium phosphate minerals. For example, in certain embodiments of interest, the cement includes both coarse and fine particle size populations of the same calcium containing mineral, e.g., α-tricalcium phosphate. In yet other embodiments, a portion, if not all of the coarse population of particles is made up of one or more different calcium containing compounds as compared to the compound making up the fine particle size population. For example, in certain embodiments, one may have a fine particle size population made up of a first calcium containing compound, e.g., α-tricalcium phosphate particles, and a coarse particle size population made up of a second calcium containing compound that differs in some way from the compound making up the first population, e.g., in terms of phase, molecular formula, solubility, radiopacity, etc. In certain embodiments, the fine and coarse particle size populations will be made up of different phases of the same is calcium containing compound, such as the same calcium phosphate containing compound. For example, the coarse and fine particle size populations could both be made up of tricalcium phosphate, but the fine particle size population could be made up of α-tricalcium phosphate while the coarse particle size population is made up of β-tricalcium phosphate particles, such that while the populations are made up of the same compound, they are made up of different phases of the same compound, where the different phases differ from each other at least in terms of solubility. In yet other embodiments, the different populations may be made up of different compounds, e.g., that differ from each other in terms of molecular formula, radiopacity, solubility, combinations thereof, etc. For example, in certain embodiments the fine particle size population is made up of α-tricalcium phosphate particles, and a coarse particle size population is made up at least partially of a different calcium containing compound, e.g., that differs in terms of at least molecular formula, if not radiopacity. For example, the second coarse population of particles may include a calcium containing compound that is not a tricalcium phosphate, such as in those embodiments where the coarse population is made up of a combination of β-tricalcium phosphate particles and particles of dolomite ($CaMgCO_3$).

For applications in which the coarse particles of the invention are employed in a cement, during use the cement dry reactants are combined with a setting fluid. Setting fluids of interest vary, and include a variety of physiologically compatible fluids, including, but not limited to: water (including purified forms thereof), aqueous alkanol or polyol solutions, e.g., glycerol, where the alkanol or polyol is present in minor amounts, such as less than 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of 0.01 to 2M, such as from 0.05 to 0.5M, and at a pH in the range of 6 to 11, such as from 7 to 9, including from 7 to 7.5; and the like.

In some instances, the cements are employed with a silicate setting fluid, i.e., a setting fluid that is a solution of a soluble silicate. By solution of a soluble silicate is is meant an aqueous solution in which a silicate compound is dissolved and/or suspended. The silicate compound may be any compound that is physiologically compatible and is soluble in water. By soluble in water is meant a concentration of 1% or greater, 2% or greater and 5% or greater, where the concentration of the silicate employed typically ranges from 0-0.1 to 20%, usually from 0.01-5 to 15% and more usually from 5 to 10%.

Silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tetramethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference in their entirety. Of particular interest in many embodiments are solutions of sodium silicate, where the manufacture of dry sodium silicate ($Na_2SiO_3$, $Na_6Si_2O_7$ and $Na_2Si_3O_7$) is described in Faith, Keyes & Clark's INDUSTRIAL CHEMICALS (1975) pp 755-761.

In certain embodiments, the setting fluid may further include an amount of phosphate ion, as described in U.S. application Ser. No. 10/462,075; the disclosure of which is herein incorporated by reference in its entirety. For example, the concentration of phosphate ion in the setting fluid may vary, but is typically at least 0.01 mol/L, such as at least 0.02 mol/L and more including at least 0.025 mol/L, where the concentration may range from 0.01 to 0.5, such as from 0.01 to 0.25, including from 0.02 to 0.2 mol/L. The desired phosphate concentration may be provided using any convenient phosphate source, such as a non-calcium-containing salt of phosphoric acid that is sufficiently soluble, e.g., $Na_3PO_4$, $Na_2HPO_4$, or $NaH_2PO_4$. Salts of other cations such as $K^+$, $NH_4^+$, etc., may also be employed.

In certain embodiments, the cements may further include an amount of an emulsifying agent, as described in U.S. application Ser. No. 11/134,051; the disclosure of which is herein incorporated by reference in its entirety. Emulsifying agents of interest include, but are not limited to: polyoxyethylene or polyoxypropylene polymers or copolymers thereof, such as polyethylene glycol and polypropylene glycol; nonionic cellulose ethers such as methylcellulose, ethylcellulose, hydroxymethylcellulose, hydroxyethylcellulose, carboxymethylcellulose, carboxyethylcellulose and hydroxypropylcellulose; additional celluloses, such as carboxymethylcellulose sodium, carboxymethylcellulose calcium, carboxymethylstarch; polysaccharides produced by microbial fermentation, such as yeast glucans, xanthan gum, β-1,3-glucans (which may be straight-chained or branched; e.g. curdlan, paramylum, pachyman, scleroglucan, laminaran); other natural polymers, e.g., gum arabic, guar gum, carrageenin, gum tragacanth, pectin, starch, gelatin, casein, dextrin, cellulose; polyacrylamide; polyvinyl alcohol; starch; starch phosphate; sodium alginate and propylene glycol alginate; gelatin; amino-containing acrylic acid copolymers and quaternization products derived therefrom; and the like.

In certain embodiments, the emulsifying agent is a cellulose ether, particularly a nonionic cellulose ether, such as carboxymethylcellulose. Carboxymethylcellulose is available from a variety of commercial sources, including but limited to, Sigma, Hercules, Fluka and Noviant. In certain embodiments, the average molecular weight of the cellulose ether is 1000 daltons or higher, such as 5000 daltons or higher, where the average molecular weight may be as high as 10,000 daltons or higher, e.g., 50,000 daltons or higher, 100,000 daltons or higher, and ranges in certain embodiments from 5,000 to 100,000 daltons, such as from 10,000 to 50,000 daltons.

The proportion of the emulsifying agent in the cement in certain embodiments ranges from 0.01 to 10% (w/w), such as from 0.05 to 2.0% (w/w).

When employed, the emulsifying agent may be included in one or both of the above liquid and dry reactant components.

In certain embodiments, the cement may further include a contrast or imaging agent, where the contrast agent may be present in one or both of the liquid and dry components, or separate therefrom until combination of all of the components to produce the flowable composition. Contrast agents of interest include, but are not limited to: the water soluble contrast agents described in U.S application Ser. No. 10/629,321, the disclosure of which is herein incorporated by reference in its entirety; and the barium apatite contrast agents described in U.S. application Ser. No. 10/851,766, the disclosure of which is herein incorporated by reference in its entirety.

One or both of the above liquid and dry reactant components may include an active agent that modulates the properties of the product into which the flowable composition prepared by the subject method sets. Such additional ingredients or agents include, but are not limited to: organic polymers, e.g., proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include, but are not limited to: osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g., NaCl, calcium sulfate; sugars, e.g., sucrose, fructose and glucose; pharmaceutically active agents, e.g., antibiotics; and the like. Additional active agents of interest include osteoclast induction agents, e.g., RANKL, as described in U.S. patent application Ser. No. 10/717,171, the disclosure of which is herein incorporated by reference in its entirety.

In using cements that comprise coarse particles of the invention, suitable amounts of the dry reactants and the setting fluid are combined to produce a settable or flowable composition. In other words, the ratio of the dry reactants to setting fluid (i.e. the liquid to solids ratio) is selected to provide for a "settable" or "flowable" composition, where by "settable" or "flowable" composition is meant a composition that goes from a first non-solid (and also non-gaseous) state to a second, solid state after setting. In some embodiments, the liquid to solids ratio is is chosen to provide for a flowable composition that has a viscosity ranging from that of milk to that of modeling clay. As such, the liquids to solids ratio employed in the subject methods may range from 0.2 to 1.0, usually from 0.3 to 0.6. Of interest in certain embodiments are methods that produce a paste composition, where the liquid to solids ratio employed in such methods typically ranges from 0.25 to 0.5, usually from 0.3 to 0.45.

As mentioned above, the requisite amounts of dry reactants and setting fluid are combined under conditions sufficient to produce the flowable product composition. As such, the dry and liquid components may be combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference in their entirety. Also of interest is the device disclosed in U.S. Pat. No. 5,980,482, the disclosure of which is herein incorporated by reference in its entirety. Of interest in certain embodiments are the storage/mixing elements disclosed in U.S. Pat. Nos. 6,375,935 and 6,719,993; as well as U.S. application Ser. Nos. 10/462,075; 10/629,321; 10/717,171; 10/851,766; 10/661,356; 10/797,907; and 10/850,985; the disclosures of which are herein incorporated by reference in their entirety.

The temperature of the environment in which combination or mixing of the dry and liquid components takes place is sufficient to provide for a product that has desired setting and strength characteristics, and may range from 0 to 50° C., usually from 20 to 30° C. Mixing takes place for a period of time sufficient for the flowable composition to be produced, and generally takes place for a period of time ranging from 15 to 120 seconds, usually from 15 to 100 seconds and more usually from 15 to 60 seconds, e.g., 15 to 50 seconds, 15 to 30 seconds, etc.

The above-described protocols result in the production of a flowable composition that is capable of setting into a calcium phosphate mineral product, as described in greater detail below, where the flowable composition is radio-opaque during, at least during implantation.

The flowable compositions produced by the above-described methods are compositions that set into a biologically compatible, and often resorbable and/or remodelable, product, where the product is characterized by including calcium phosphate molecules not present in the initial reactants, i.e., that are the product of a chemical reaction among the initial reactants.

The term flowable is meant to include paste-like compositions, as well as more liquid compositions. As such, the viscosity time of the subject flowable compositions, defined as time periods under which the mixed composition injects through a standard Luer-lok fitting after mixing, typically ranges up to 10 minutes, usually up to 7 minutes, such as up to 4 minutes. Of interest in certain embodiments are paste compositions that have an injectable viscosity that injects in a time period ranging up to 5 minutes, such as up to 4 minutes. Pastes that stay paste-like for longer period may be displaced by bleeding bone once implanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many embodiments, the calcium phosphate mineral is one that is generally poorly crystalline, so as to be resorbable, and often, remodelable, over time when implanted into a physiologically site. The calcium to phosphate ratio in the product may vary depending on particular reactants and amounts thereof employed to produce it, but typically range from 2:1 to 1.33:1, usually from 1.8:1 to 1.5:1 and more usually from 1:7:1 to 1.6:1. Of particular interest in many embodiments are apatitic products, which apatitic products have a calcium to phosphate ratio ranging from 2.0:1 to 1.33:1, including both hydroxyapatite and calcium deficient analogs thereof, including carbonate substituted hydroxyapatite (i.e. dahilite), etc. The subject paste-like composition is, in certain embodiments, one that is capable of setting into a hydroxyapatitic product, such as a carbonated hydroxyapatite, i.e. dahilite, having a carbonate substitution of from 2 to 10%, usually from 2 to 8% by weight of the final product.

The period of time required for the compositions to harden or "set" may vary. By set is meant: the Gilmore Needle Test (ASTM C266-89), modified with the cement submerged under 37° C. physiological saline. The set times of the subject cements may range from 30 seconds to 30 minutes, and will usually range from 2 to 15 minutes and more usually from 4 to 12 minutes. In many embodiments, the flowable composition sets in a clinically relevant period of time. By clinically relevant period of time is meant that the paste-like composition sets in less than 20 minutes, usually less than 15 minutes and often in less than 10 minutes, where the composition remains flowable for 1 minute or longer, usually 2 minutes or longer and, in many embodiments, for 5 minutes or longer following combination or mixture of the precursor liquid and dry cement components.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of 20 or greater, usually 40 and greater, usually 50 or greater MPa, as measured by the assay described in Morgan, E F et al., 1997, Mechanical Properties of Carbonated Apatite Bone Mineral Substitute: Strength, Fracture and Fatigue Behavior. J. Materials Science: Materials in Medicine. V. 8, pp 559-570, where the compressive strength of the final apatitic product may be as high as 60 MPa or higher. Inclusion of the silicate in the setting liquid allows lower liquid to solids ratios to be employed which results in significantly higher compressive strengths. Compressive strengths can be obtained that range as high 100 to 200 MPa. In certain embodiments, the resultant product has a tensile strength of 0.5 MPa or greater, such as 1 MPa or greater, including 5 MPa or greater, 10 MPa or greater, e.g., from 0.5 to 10 MPa.

In many embodiments, the resultant product is stable in vivo for extended is periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for 4 months or longer, 6 months or longer, 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for 4 months or longer, 6 months or longer, 1 year or longer, e.g., 2.5 years, 5 years, etc.

In certain embodiments of interest, the product that is produced is a composite product, which includes some unreacted particles, e.g., from the coarse population, present in the final product. In certain of the embodiments where such a cement is implanted into an in vivo site, the unreacted particles may dissolve (e.g., via resorption) over time leaving a porous structure at the implant site, where the porous structure remains until it is remodeled. In certain embodiments, the remaining coarse particles in the composite may have a different radiopacity than the remainder of the product, e.g., where at least a portion of the coarse particles in the cement were dolomite.

In many embodiments, the flowable paste-like composition is capable of setting in a fluid environment, such as an in vivo environment at a bone repair site. As such, the flowable paste composition can set in a wet environment, e.g., one that is filled with blood and other physiological fluids. Therefore, the site to which the flowable composition is administered during use need not be maintained in a dry state.

In certain embodiments, the subject cement compositions may be seeded with any of a variety of cells, as described in published U.S. Patent Publication No. 20020098245, the disclosure of which is herein incorporated by reference in its entirety.

In addition, in certain embodiments the compositions include demineralized bone matrix, which may be obtained typically in a lyophilized or gel form and is is combined with the cement composition at some prior to implantation. A variety of demineralized bone matrixes are known to those of skill in the art and any convenient/suitable matrix composition may be employed.

In certain embodiments, the cements may include one or more collections of contrast particles (for example, for use as tracers during use of the cement), e.g., as described in U.S. Pat. No. 6,273,916 or U.S. application Ser. Nos. 10/629,321 and 10/851,766; the disclosures of which are herein incorporated by reference in their entirety.

One cement composition in which the tricalcium phosphate coarse particles of the invention find use is the composition described in PCT application serial no. PCT/US2005/026369 and published as WO/2006/014886, the disclosure of which is herein incorporated by reference.

Applications

Flowable compositions produced from cements of the invention, e.g., as described above, find use in applications where it is desired to introduce a flowable material capable of setting up into a solid calcium phosphate product into a physiological site of interest, such as in dental, craniomaxillofacial and orthopedic applications. In orthopedic applications, the cement will generally be prepared, as described herein, and introduced to a bone repair site, such as a bone site comprising cancellous and/or cortical bone.

Other orthopedic applications in which the cements prepared by the subject system find use include, but are not limited to, the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific dental, craniomaxillofacial and orthopedic indications in which the subject invention finds use include, but are not limited to, those described in U.S. Pat. No. 6,149,655, the disclosure of which is herein incorporated by reference in its entirety. In addition to these particular applications described in this U.S. Patent, the subject cement compositions also find use in applications where a sternotomy has been performed. Specifically, the subject cements find use in the closure process of a sternotomy, where the bone fragments are rejoined and wired together, and any remaining cracks are filled with the subject cement. In yet other embodiments, the subject compositions find use in drug delivery, where they are capable of acting as long lasting drug depots following administration to a physiological site. See e.g. U.S. Pat. Nos. 5,904,718 and 5,968,253; the disclosures of which are herein incorporated by reference in their entirety.

Representative applications of interest also include, but are not limited to: those described in U.S. Pat. Nos. 6,375,935 and 6,719,993; as well as U.S. application Ser. Nos. 10/462,075; 10/629,321; 10/717,171; 10/851,766; 10/661,356; 10/797,907; and 10/850,985; the disclosures of which are herein incorporated by reference in their entirety.

Kits

Also provided are kits that include the subject cements, where the kits at least include a dry particulate composition which includes a tricalcium phosphate coarse particle composition, as described above. One embodiment provides a kit comprising a setting fluid and a dry reactant component comprising a tricalcium phosphate coarse particle composition comprising tricalcium phosphate particles ranging in size from 38 to 212 µm. The coarse particles may include an alkali metal ion in an amount ranging from 1500 to 2500 ppm. The kit can also include a fine calcium phosphate particulate composition having a mean particle size of less than 8 µm and narrow particle size distribution.

In certain embodiments, the kits further include a liquid component. When both components are present, the dry and liquid components may be present in separate containers in the kit, or some of the components may be combined into one container, such as a kit wherein the dry components are present in a first container and the liquid components are present in a second container, where the containers may or may not be present in a combined configuration, as described in U.S. Pat. No. 6,149,655, the disclosure of which is herein incorporated by reference in its entirety. In addition to the cement compositions, the subject kits may further include a number of additional reagents, e.g., cells (as described above, where the composition is to be seeded), protein reagents (as described above), and the like.

In certain embodiments, the subject cements may be kitted as described in U.S. Pat. No. 6,273,916, the disclosure of which is herein incorporated by reference in its entirety, e.g., packaged in a kit with at least two different sterilized pouches (or analogous compartments) of cement that may independently used at the same or different times, where each pouch may include the same or different cement formulation, e.g., where the cements may differ in terms of contrast characteristics.

In certain embodiments, the kits may further include mixing and/or delivery elements, e.g., mortar and pestle, spatula, etc., which elements find use in, e.g., the preparation and/or delivery of the cement composition.

In addition to above-mentioned components, the subject kits typically further include instructions for using the components of the kit to practice the subject methods. The instructional material may also be instructional material for using the cement compositions, e.g., it may provide surgical techniques and principals for a particular application in which the cement is to be employed. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Systems

Also provided are systems that find use in practicing the subject methods, as described above. The subject systems at least include dry and liquid components of a cement, as described above, and a mixing element. In certain embodiments, the systems may further include additional agents, e.g., contrast agents, active agents, etc., as described above.

The following examples are offered by way of illustration and not by way of limitation.

Experimental

I. Process of Forming Coarse Particles

Process A provides a preparation method for forming a tricalcium phosphate particulate composition as described in PCT application serial no. PCT/US2005/026369 and published as WO/2006/014886. Process A is provided as a comparative example for Processes B and C, which processes are embodiments of the coarse particle preparation methods of the invention.

Process B and Process C provided high yields of coarse particles as compared to Process A. Both processes yielded particles that are same in phase (95-97% α-TCP, 3-5% HA), have similar morphology (they are irregularly shaped is particles) and have no major impurity incorporation but have different densities and hardness. Process B utilizes a step of disc milling after formation of hydroxyapatite. Process C utilizes a step of pelletizing after formation of hydroxyapatite. Table 1 shows steps that are common to Processes A-C. Tables 2-4 show the successive steps for Processes A-C, respectively.

TABLE 1

Common Steps to Processes A-C

| Step | Description of step |
|---|---|
| 1 | Weigh 1414.1 g ± 1.0 g DCPA and 520.2 g ± 1.0 g Calcite in a container |
| 2 | Blend on jar mill using '100' setting |
| 3 | Weigh 1395.2 g ± 1.0 g DI $H_2O$ into a beaker Carefully introduce blended powder into beaker |
| 5 | Mix using blender on low setting |
| 6 | Fill tray molds with slurry to depth of ¾ inches |
| 7 | Place trays in oven at 110° C. |
| 8 | Take the trays out and let them cool to room temperature |
| 9 | Place cakes in alumina trays for firing |
| 10 | Fire the cakes at 1425° C. |
| 11 | Quench the cakes with a stainless steel rod |
| 12 | Let the quenched material cool to room temperature |

TABLE 2

Process A

| Step | Description of step |
|---|---|
| 13 | Perform Sieving-Grinding-Sieving cycles to reduce particles to appropriate sizes |
| 14 | The process yields 17% particles of 38-212 μm 185 grams of particles of 38-212 μm 915 grams of particles of <38 μm |

TABLE 3

Process B

| Step | Description of step |
|---|---|
| 13 | Put the material into disc mill (3 times) at a gap setting of 254 μm in order to obtain <38 μm particle size |
| 14 | Jet Mill above material at a feed rate of 275 to obtain 2 μm jet milled impact |
| 15 | Place the jet milled powder in the stainless steel bucket of the blender |
| 16 | Prepare sodium phosphate solution by dissolving 11.445 grams in 336 grams DI $H_2O$ |
| 17 | Add the sodium phosphate solution into the powder and mix (Formation of Hydroxyapatite) |
| 18 | Scrape the paste from the container |
| 19 | Dry at 140° C. for 2 hours and cool |
| 20 | Sieve the powders |
| 21 | Disc Mill >212 μm powders at a gap setting of 500 μm (Disc Mill) |
| 22 | Sieve the disc milled powder |
| 23 | Repeat disc mill-sieving cycle until all the powder is grinded to <212 μms |
| 24 | Fire the powders at 1425° C. for 2 hour (Sintering) |
| 25 | Quench the powders by light pressing by a quencher |
| 26 | Sieve the fired powders (Start of Mechanical manipulation) |
| 27 | Grind the >212 μm fraction in an alumina mortar |
| 28 | Sieve the grinded powders |
| 29 | Repeat grinding-sieving process until all the powder is <212 μm |
| 30 | The process yields 80% particles of 38-212 μm 744 grams particles of 38-212 μm 186 grams of waste <38 μm |

TABLE 4

Process C

| Step | Description of step |
|---|---|
| 13 | Put the material into disc mill (3 times) at a gap setting of 254 μm in order to obtain <38 μm particle size |
| 14 | Place the <38 μm powder in the stainless steel bucket of the blender |
| 15 | Prepare sodium phosphate solution by dissolving 11.2 grams in 465 grams DI $H_2O$ |
| 16 | Add the sodium phosphate solution into the powder and mix (Formation of Hydroxyapatite) |
| 17 | Scrape the attached paste from the container |
| 18 | Dry at 140° C. overnight and cool |
| 19 | Disc Mill the powders at a gap setting of 1500 μm |
| 20 | Send the powders for pellet making (Pelletize) |
| 21 | Receive the pellets from pellet making |
| 22 | Fire the pellets at 1425° C. for 2 hours (Sintering) |
| 23 | Quench by spreading the pellets on a stainless steel tray |
| 24 | Grind the pellets in the disc mill at a gap setting of 500 μm (Start of Mechanical manipulation) |
| 25 | Sieve the disc milled powder |

TABLE 4-continued

Process C

| Step | Description of step |
|---|---|
| 26 | Disc mill the >212 μm powders at a gap setting of 254 μm |
| 27 | Sieve the disc milled powder |
| 28 | Disc mill the >212 μm powders at a gap setting of 254 μm |
| 29 | Sieve the disc milled powder |
| 32 | The process yields 60% particles of 38-212 μm 570 grams particles of 38-212 μm 380 grams of waste <38 μm |

Results (a) XRD Comparison

Figure 1:
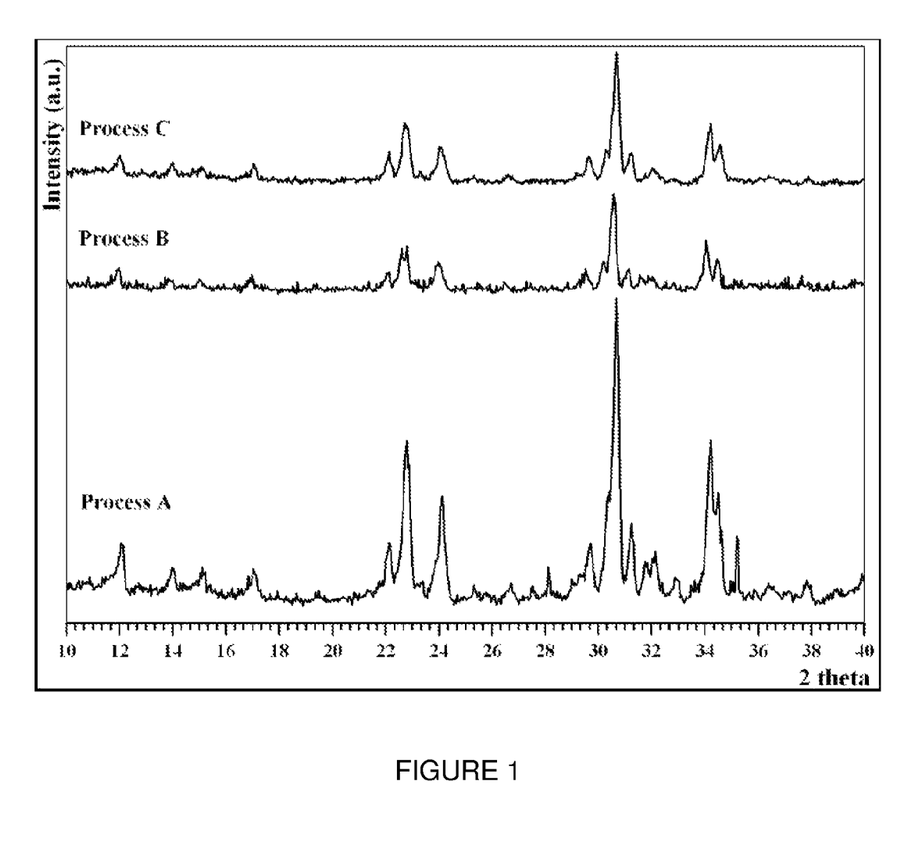
FIG. 1 shows an X-ray diffraction of material synthesized from Process A, Process B, and Process C, as described in greater detail in the Experimental Section, below.

FIG. 1 shows X-ray diffraction of the materials synthesized by Process A, Process B, and Process C.

Table 5 shows a Rietveld analysis of the materials synthesized by Process A, Process B, and Process C.

TABLE 5

Rietveld Analysis of Materials Synthesized by Processes A-C

| Sample | Alpha-TCP | Beta-TCP | HA |
|---|---|---|---|
| Process A | ~95 | <1 | ~4-5 |
| Process B | ~94 | <1 | ~5-6 |
| Process C | ~97 | <1 | ~2-3 |

(b) FE-SEM Micrographs

Figure 2A:
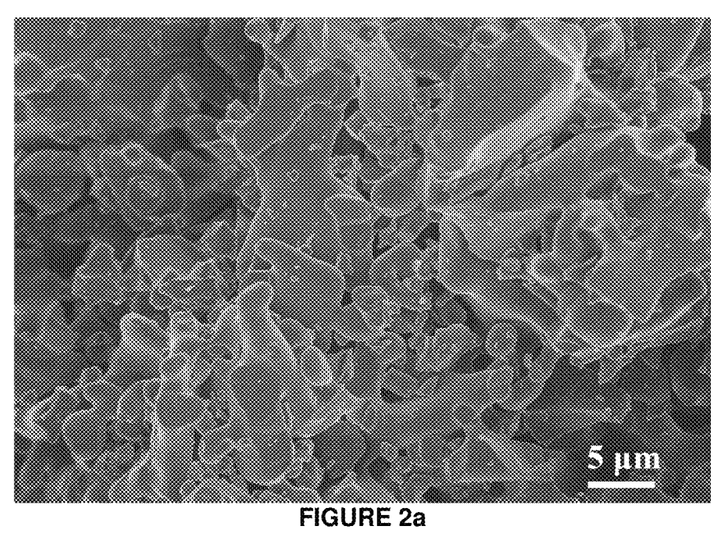
FIG. 2a shows an SEM micrograph of particles obtained from Process A that are 38-106 µm.
Figure 2B:
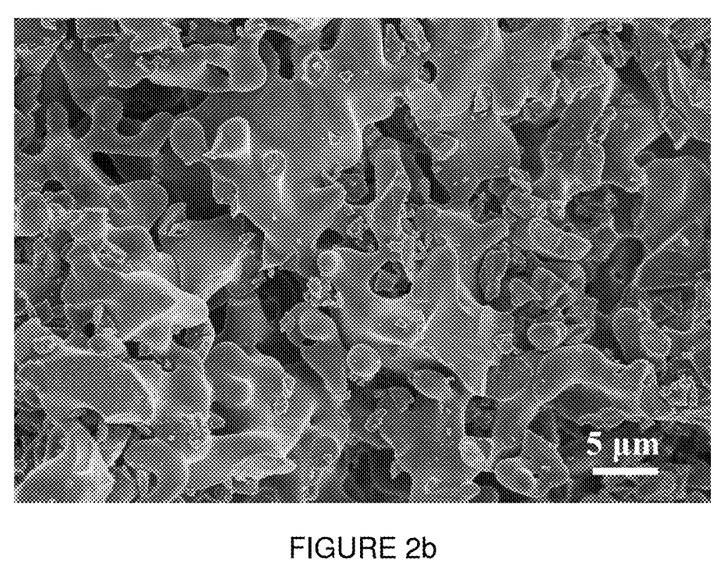
FIG. 2b shows an SEM micrograph of particles obtained from Process A that are 106-212 µm.

FIGS. 2a and 2b show morphology of particles formed from Process A. FIG. 2a shows an SEM micrograph of particles obtained from Process A that are 38-106 μm. FIG. 2b shows an SEM micrograph of particles obtained from Process A that are 106-212 μm. The coarse particles are porous in structure. The coarse particles from Process A are formed when small particles loosely bind to each other by forming necks during sintering. The coarse particles from Process A are weak and are observed to break into 30 μm sized particles during light ultrasonication.

Figure 3A:
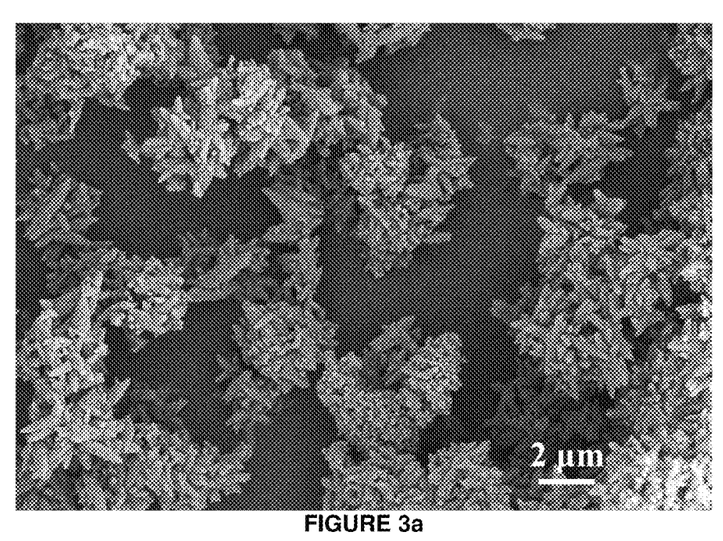
FIG. 3a shows calcite morphology.
Figure 3B:
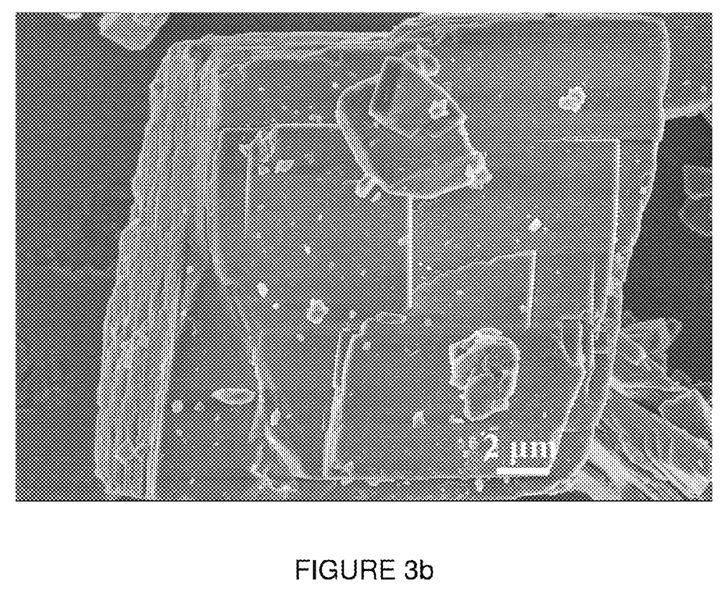
FIG. 3b shows monetite morphology.

FIG. 3a shows morphology of calcite. In FIG. 3a, there is a needle-shaped morphology. The needles are at an average of 2 μm in length and 0.25 μm in diameter. FIG. 3b shows morphology of monetite. In FIG. 3b, there is a rectangular-shaped plate-like morphology. There are different sized crystals.

Figure 4:
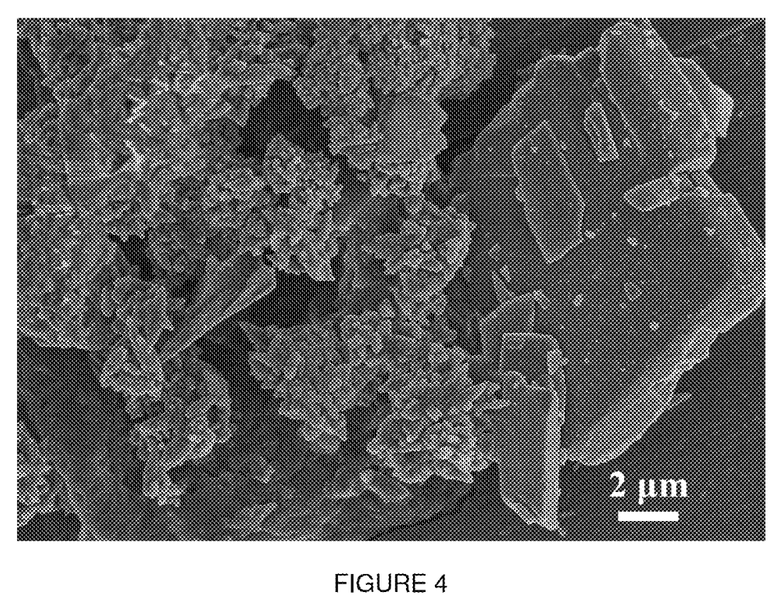
FIG. 4 shows an SEM micrograph of material obtained from Process A after the blending step.

FIG. 4 shows SEM analysis of particles formed from Process A, after a blending step (step 5). There is a homogeneous mixture of calcite needles and monetite crystals.

Figure 5A:
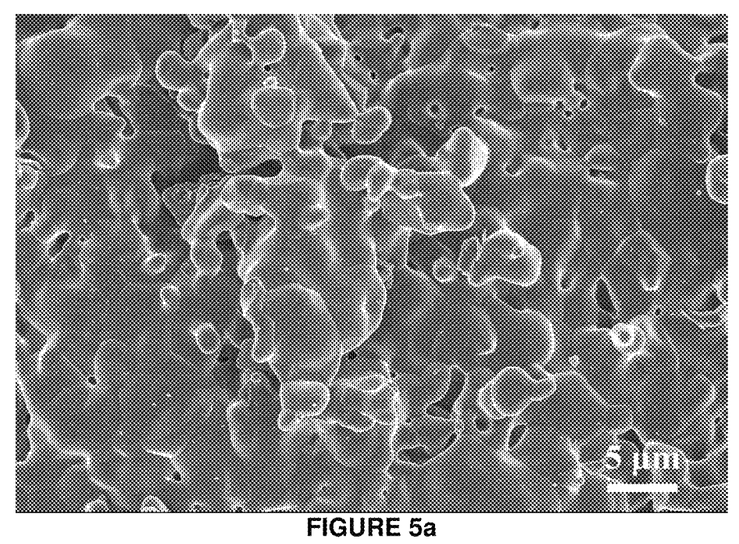
FIG. 5a shows an SEM micrograph of particles obtained from Process B that are 38-106 µm.
Figure 5B:
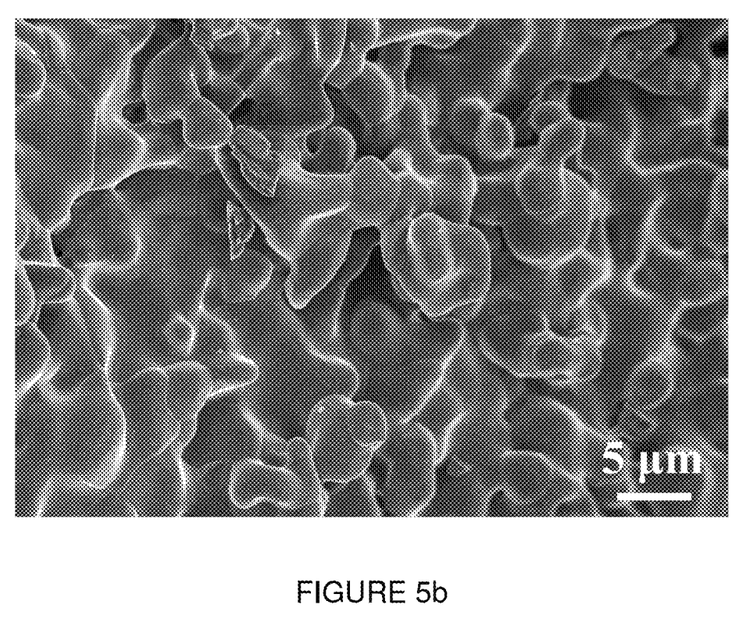
FIG. 5b shows an SEM micrograph of particles obtained from Process B that are 106-212 µm.

FIGS. 5a and 5b show morphology of particles formed from Process B. FIG. 5a shows an SEM micrograph of particles obtained from Process B that are 38-106 μm. FIG. 5b shows an SEM micrograph of particles obtained from Process B that are 106-212 μm. The coarse particles are very dense and strong. The use of coarse particles formed from Process B in a settable/flowable composition gives higher setting and tensile values. For an impact formulation, a tensile strength of around 8 MPa is achieved by coarse particles formed from Process B, whereas a tensile strength of around 4.5 MPa is achieved by coarse particles formed from Process A.

Figure 6:
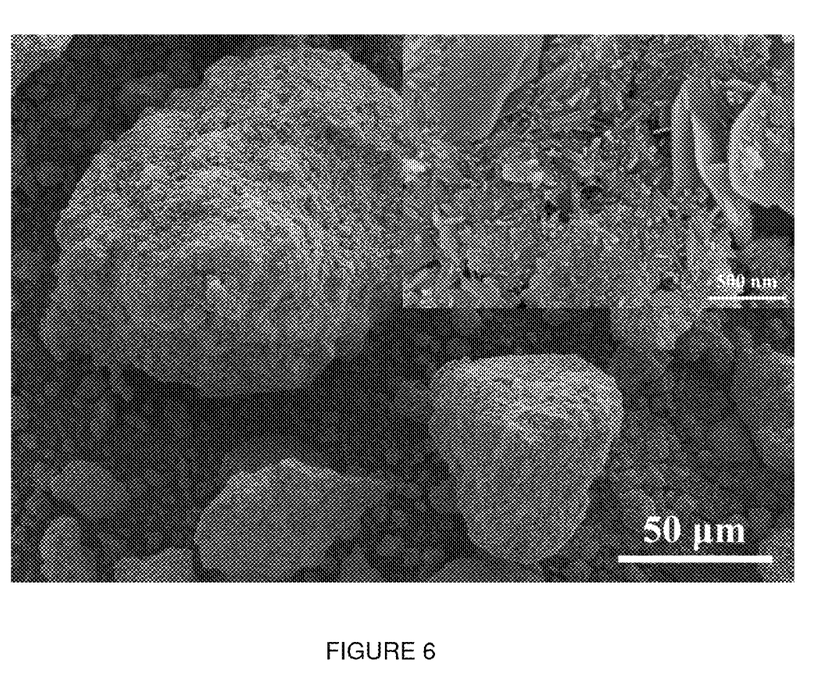
FIG. 6 shows an SEM micrograph of material obtained from Process B before the firing step.

FIG. 6 shows SEM analysis of particles formed from Process B before the firing step (step 10). In Process B, the cement reaction occurs, thus forming small interlocking needles as seen in high magnification.

Figure 7:
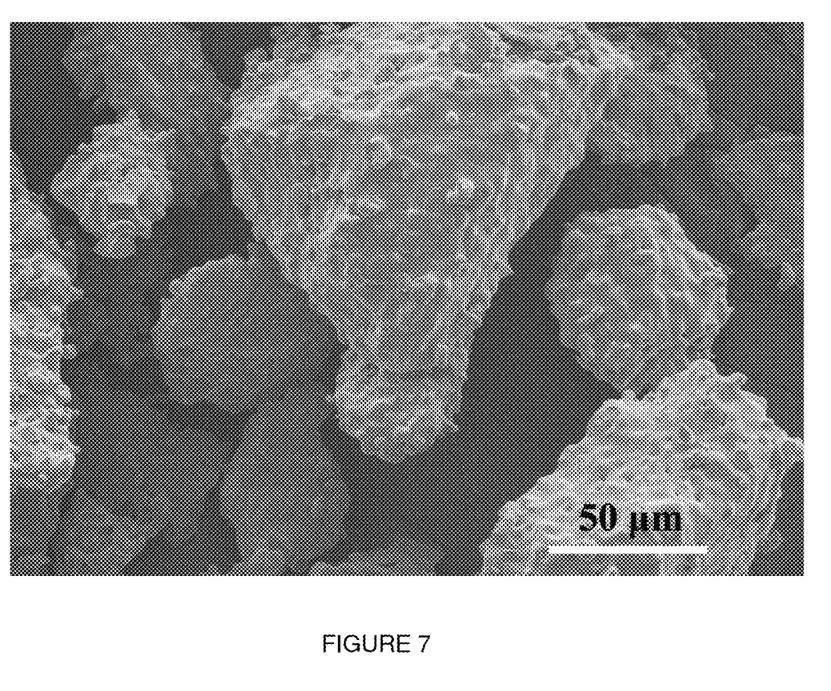
FIG. 7 shows an SEM micrograph of material obtained from Process B after the firing step.

FIG. 7 shows SEM analysis of particles formed from Process B after the firing step (step 10). The coarse particles are dense and can withstand ultrasonication without breaking.

Figure 8:
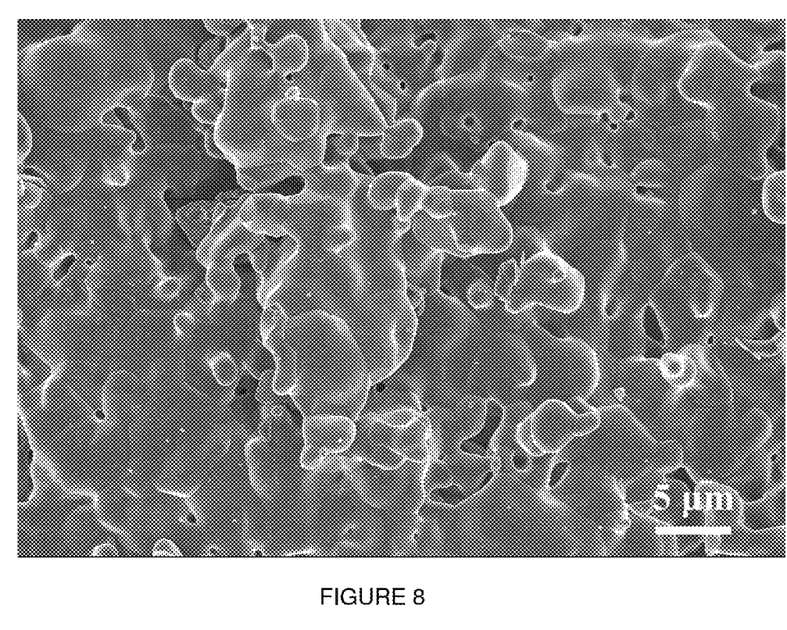
FIG. 8 shows an SEM micrograph of material obtained from Process B after is the firing step.

FIG. 8 shows SEM analysis of particles formed from Process B after the firing step (step 10). Only small percentage of surface porosity is formed due to either evaporation of gases or conversion of 4/5 grains into 3 grains.

Figure 9A:
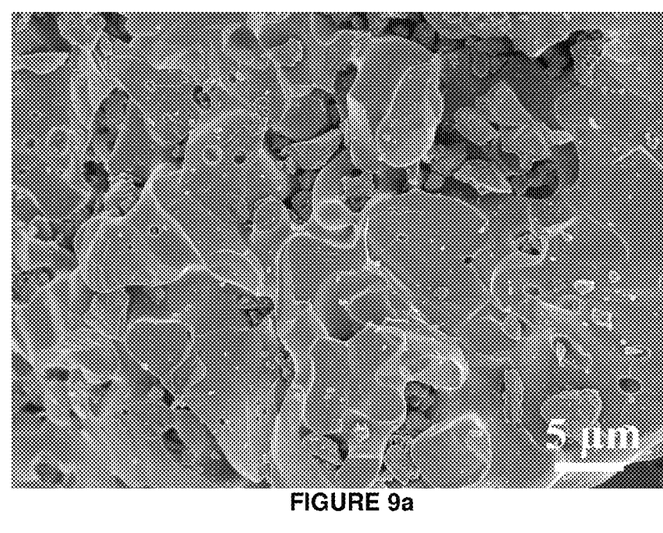
FIG. 9a shows an SEM micrograph of particles obtained from Process C that are 38-106 µm.
Figure 9B:
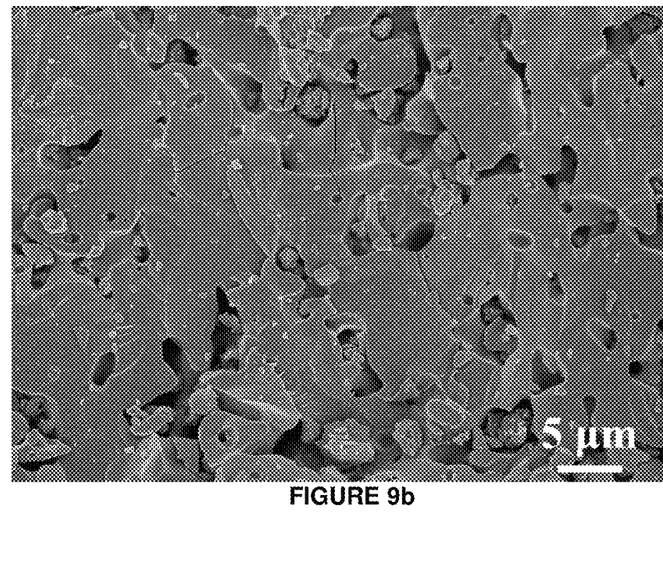
FIG. 9b shows an SEM micrograph of particles obtained from Process C that are 106-212 µm.

FIGS. 9a and 9b show morphology of particles formed from Process C. FIG. 9a shows an SEM micrograph of particles obtained from Process C that are 38-106 μm. FIG. 9b shows an SEM micrograph of particles obtained from Process C that are 106-212 μm. The coarse particles are very dense and strong. The use of coarse particles formed from Process C in a settable/flowable composition gives higher setting and tensile values. The surface area of the particles formed from Process C is similar to the surface area of the particles formed from Process A.

(c) Inductively Coupled Plasma-Atomic Emission Spectroscopy (ICP-AES)

The ICP-AES analysis in Table 6 shows no major differences in elemental analysis of the coarse particles from Processes A-C. For the Process B and Process C, only sodium percentage was higher than Process A. This sodium amount comes from SPMA that was added to α-TCP for converting to hydroxyapatite.

TABLE 6

ICP-AES Analysis of coarse particles synthesized by different processes

| | Process A | | Process B | | Process C | |
|---|---|---|---|---|---|---|
| Element | 38-106 μm | 106-212 μm | 38-106 μm | 106-212 μm | 38-106 μm | 106-212 μm |
| P (%) | 20.02 | 20.1 | 19.44 | 19.1 | 19.05 | 19.61 |
| K (%) | 0.01 | 0 | 0.01 | 0.01 | 0.01 | 0.01 |
| Ca (%) | 39.57 | 40 | 38.2 | 37.13 | 38.05 | 38.04 |
| Mg (%) | 0.08 | 0.08 | 0.07 | 0.07 | 0.12 | 0.12 |
| Zn (ppm) | 7.2588 | 6.4048 | 8.4 | 6.91 | 5.8 | 8.7 |
| Cu (ppm) | 0 | 0 | 0 | 0 | 1.77 | 1.39 |
| Mn (ppm) | 6.1219 | 6.9635 | 7.21 | 8.22 | 6.49 | 10.37 |
| Fe (ppm) | 129.63 | 88.889 | 108.4 | 99.78 | 136.36 | 157.25 |
| S (%) | 0.07 | 0.01 | 0.002 | 0 | 0.01 | 0.01 |
| Na (ppm) | 26.51 | 27.65 | 1992 | 2110 | 1722 | 1798 |
| B (ppm) | 5.399 | 6.351 | 15.27 | 11.9 | 10.11 | 11.18 |
| Al (ppm) | 84.36 | 56.24 | 116.8 | 115.8 | 159.95 | 227.9 |
| N (%) | 0 | 0 | 0 | 0 | 0 | 0 |
| Si (ppm) | 149.5 | 152 | 103 | 112.5 | 117.5 | 97 |
| Zr (ppm) | 24 | 13.5 | 40.5 | 34.5 | 25 | 11.5 |

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of making a tricalcium phosphate coarse particle composition, said method comprising:
   (a) converting an initial tricalcium phosphate particulate composition to hydroxyapatite;
   (b) sintering said hydroxyapatite to produce a second tricalcium phosphate composition; and
   (c) mechanically manipulating said second tricalcium phosphate composition to produce a tricalcium phosphate coarse particle composition, wherein said coarse particles comprise sodium in an amount ranging from 1500 to 2500 ppm.

2. The method according to claim 1, wherein said initial tricalcium phosphate particulate composition is converted to hydroxyapatite by combining said initial tricalcium phosphate particulate composition with an alkali metal phosphate solution.

3. The method according to claim 2, wherein said alkali metal phosphate solution is a sodium phosphate solution.

4. The method according to claim 1, wherein after step (a), said hydroxyapatite is milled before sintering in step (b).

5. The method according to claim 1, wherein after step (a), said hydroxyapatite is pelletized before sintering in step (b).

6. The method according to claim 1, wherein said initial tricalcium phosphate particulate composition is prepared by:
   (a) combining dicalcium phosphate anhydrous, calcite and water to produce a paste composition;
   (b) sintering said paste composition to produce a sintered product; and
   (c) mechanically disrupting said sintered product to produce said initial tricalcium phosphate particulate composition.

7. The method according to claim 1, wherein said tricalcium phosphate coarse particle composition comprises a-tricalcium phosphate particles.

8. The method according to claim 1, wherein said method yields a composition that is 25% or more coarse particles.

9. The method according to claim 1, wherein said method yields a composition that is 50% or more coarse particles.

10. The method according to claim 1, wherein said method yields a composition that is 60% or more coarse particles.

11. The method according to claim 1, wherein said method yields a composition that is 80% or more coarse particles.

12. The method according to claim 1, wherein said tricalcium phosphate coarse particle composition comprises particles ranging in size from 38 to 212 μm.

13. A tricalcium phosphate coarse particle composition produced according to the method of claim 1.

14. A tricalcium phosphate coarse particle composition comprising tricalcium phosphate particles ranging in size from 38 to 212 μm, wherein said particles comprise sodium in an amount ranging from 1500 to 2500 ppm.

15. The method according to claim 1, wherein said sintering comprises heating said hydroxyapatite to temperature ranging from 1300 to 1500° C.

16. The method according to claim 1, wherein said tricalcium phosphate coarse particle composition comprises particles that are 95-97% α-TCP.

17. The method according to claim 1, wherein said method further comprises combining said tricalcium phosphate coarse particle composition with a fine calcium phosphate particulate composition to produce a dry reactant cement component.

18. The method according to claim 17, wherein said fine calcium phosphate particulate composition has a mean particle size of less than 8 μm and narrow particle size distribution.

19. The method according to claim 17, wherein the ratio of the mass of the fine particle composition to the total mass of the tricalcium phosphate coarse particle composition ranges from 1 to 10.

* * * * *